「US011076954B2」

(12) United States Patent
Najm et al.

(10) Patent No.: US 11,076,954 B2
(45) Date of Patent: Aug. 3, 2021

(54) GRADUALLY-EXPANDABLE STENT APPARATUS AND METHOD

(71) Applicant: THE CLEVELAND CLINIC FOUNDATION, Cleveland, OH (US)

(72) Inventors: Hani Najm, Beachwood, OH (US); Kelly B. Emerton, Bay Village, OH (US); Alex Lewis, West Lafayette, IN (US); Justin Metcalf, West Lafayette, IN (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 119 days.

(21) Appl. No.: 16/136,694

(22) Filed: Sep. 20, 2018

(65) Prior Publication Data
US 2019/0083255 A1    Mar. 21, 2019

Related U.S. Application Data (60) Provisional application No. 62/561,284, filed on Sep. 21, 2017.

(51) Int. Cl.
*A61F 2/24* (2006.01)
*A61F 2/91* (2013.01)

(52) U.S. Cl.
CPC .......... *A61F 2/2418* (2013.01); *A61F 2/2409* (2013.01); *A61F 2/91* (2013.01);
(Continued)

(58) Field of Classification Search
CPC .... A61F 2/2409; A61F 2/2418; A61F 2/2445; A61F 2/2454; A61F 2002/825;
(Continued)

(56) References Cited

U.S. PATENT DOCUMENTS 9,381,103 B2    7/2016  Abunassar
9,427,339 B2    8/2016  Shalev
(Continued)

FOREIGN PATENT DOCUMENTS

EP      2853237 A1     4/2015
WO   2009/108355 A1    9/2009
(Continued)

OTHER PUBLICATIONS

PCT International Search Report and Written Opinion for corresponding PCT Application Serial No. PCT/US2018/051934, dated Feb. 25, 2019, pp. 1-16.

*Primary Examiner* — Paul B Prebilic
(74) *Attorney, Agent, or Firm* — Tarolli, Sundheim, Covell & Tummino LLP (57) ABSTRACT

A gradually-expandable stent includes a base ring completely encircling a central valve-accepting area. A plurality of uprights is provided. Each upright includes two longitudinally extending upright struts. Each upright strut has a strut base directly connected to the base ring and a strut tip directly attached to the other strut tip of the upright strut at a rounded upright apex. The upright apex is longitudinally spaced from the base ring. At least one expansion feature is associated with the base ring and gradually expands to enlarge the central valve-accepting area toward a maximum valve-accepting area responsive to growth of the patient over an extended dwell time.

19 Claims, 11 Drawing Sheets (52) U.S. Cl.
CPC .......... *A61F 2210/0004* (2013.01); *A61F 2220/0033* (2013.01); *A61F 2250/001* (2013.01); *A61F 2250/0031* (2013.01); *A61F 2250/0063* (2013.01); *A61F 2250/0065* (2013.01); *A61F 2250/0071* (2013.01); *A61F 2250/0082* (2013.01)

(58) Field of Classification Search
CPC ...... A61F 2210/0004; A61F 2220/0033; A61F 2250/001; A61F 2250/0031; A61F 2250/0082; A61F 2250/0071
See application file for complete search history.

(56) References Cited

U.S. PATENT DOCUMENTS

| | | | |
|---|---|---|---|
| 2001/0021874 A1 | 9/2001 | Carpentier et al. | |
| 2003/0065386 A1 | 4/2003 | Weadock | |
| 2008/0114452 A1* | 5/2008 | Gabbay | A61F 2/2412 623/2.42 |
| 2009/0264989 A1* | 10/2009 | Bonhoeffer | A61F 2/2412 623/1.26 |
| 2013/0274872 A1* | 10/2013 | Vesely | A61F 2/2412 623/2.17 |
| 2016/0220361 A1* | 8/2016 | Weber | A61F 2/2412 |
| 2017/0000603 A1* | 1/2017 | Conklin | A61F 2/2409 |
| 2019/0029811 A1* | 1/2019 | Bishop | A61F 2/2418 |
| 2020/0383779 A1* | 12/2020 | Conklin | A61F 2/2418 |

FOREIGN PATENT DOCUMENTS

| | | | |
|---|---|---|---|
| WO | 2012/018779 | A2 | 2/2012 |
| WO | 2016/071823 | A1 | 5/2016 |
| WO | 2017/139380 | A1 | 8/2017 |

* cited by examiner

GRADUALLY-EXPANDABLE STENT APPARATUS AND METHOD

RELATED APPLICATION

This application claims priority from U.S. Provisional Application No. 62/561,284, filed 21 Sep. 2017, the subject matter of which is incorporated herein by reference in its entirety.

TECHNICAL FIELD

This disclosure relates to an apparatus and method for use of a gradually-expandable stent and, more particularly, to a method for use and an apparatus for a gradually annularly-expandable stent for supporting a pulmonary autograft in a selected one of the mitral and aortic positions relative to a heart valve replacement procedure for a growth-potential patient.

BACKGROUND

The Ross Procedure is often very effective for treating damaged aortic or mitral valves. The aortic or mitral valve is similar in shape to the patient's own pulmonary valve. The pulmonary valve can usually be "swapped out" with the damaged aortic or mitral valve, with a donor valve taking the place of the original pulmonary valve.

The pulmonary valve is usually under less stress than the aortic or mitral valve because the right pumping chamber does not need to generate as much force to push blood to the lungs. Therefore, a replacement donor valve can be more likely to succeed in the pulmonary position than in the aortic or mitral position.

Even after the pulmonary valve is moved into the aortic valve position, it can continue to grow normally in a child who is not fully grown, or another type of growth-capable patient, and the pulmonary valve can handle the high volume of blood flow in the mitral or aortic position.

However, it may be desirable for the pulmonary valve to be attached to a valve annulus stent, to assist with installing and supporting the pulmonary valve. As the patient grows, this stent does not grow along with the pulmonary valve. Potentially, additional surgical procedures may be needed as the patient grows, to replace the original stent with a larger version to continue to support the transplanted pulmonary valve, or to remove the original stent and thus reduce the structural support for the transplanted pulmonary valve. These additional surgical procedures (to address/correct stent size as the patient grows) present unwanted risk to the patient and may ultimately contribute to adverse patient outcomes.

SUMMARY

In an aspect, a gradually-expandable stent is described. A base ring completely encircles a central valve-accepting area. A plurality of uprights is provided. Each upright includes two longitudinally extending upright struts. Each upright strut has a strut base directly connected to the base ring and a strut tip directly attached to the other strut tip of the upright strut at a rounded upright apex. The upright apex is longitudinally spaced from the base ring. At least one expansion feature is associated with the base ring and gradually expands to enlarge the central valve-accepting area toward a maximum valve-accepting area responsive to growth of the patient over an extended dwell time.

In an aspect, a gradually-expandable stent is described. A base ring completely encircles a central valve-accepting area. A plurality of uprights is provided. Each upright includes two longitudinally extending upright struts. Each upright strut has a strut base directly connected to the base ring and a strut tip directly attached to the other strut tip of the upright strut at a rounded upright apex. The upright apex is longitudinally spaced from the base ring. At least one external ring feature extends coaxially with the base ring and is spaced laterally outside at least one upright. At least one expansion feature is associated with at least one of the external ring feature and the base ring. Each expansion feature gradually expands to enlarge the central valve-accepting area toward a maximum valve-accepting area responsive to growth of the patient over an extended dwell time.

In an aspect, a method of supporting a pulmonary autograft in a selected one of the mitral and aortic positions relative to a heart valve replacement procedure for a growth-potential patient is provided. A gradually-expandable stent is provided. The gradually-expandable stent includes a base ring completely encircling a central valve-accepting area. A plurality of uprights is provided. Each upright includes two longitudinally extending upright struts. Each upright strut has a strut base directly connected to the base ring and a strut tip directly attached to the other strut tip of the upright strut at a rounded upright apex. The upright apex is longitudinally spaced from the base ring. At least one expansion feature is associated with the base ring and is configured for selective actuation to enlarge a circumference of the base ring. At least one pulmonary autograft valve commissure is attached to an upright to secure the pulmonary autograft within the central valve-accepting area. Each upright is attached to a heart tissue at the selected one of the mitral and aortic portions to suspend the pulmonary autograft in a replacement position for a selected mitral or aortic valve. The at least one expansion feature is gradually actuated to enlarge the central valve-accepting area toward a maximum valve-accepting area responsive to growth of the patient over an extended dwell time.

BRIEF DESCRIPTION OF THE DRAWINGS

For a better understanding, reference may be made to the accompanying drawings, in which:

FIGS. 14-20 are side views of optional alternate configurations of components of any aspect of the invention;

DESCRIPTION OF ASPECTS OF THE DISCLOSURE

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the terms "treat" or "treating" can refer to therapeutically regulating, preventing, improving, alleviating the symptoms of and/or reducing the effects of a heart valve defect (acquired or congenital). As such, treatment also includes situations where a heart valve defect, or at least a symptom associated therewith, is completely inhibited, e.g., prevented from happening or stopped (e.g., terminated) such that the subject no longer suffers from the heart valve defect, or at least the symptom(s) associated therewith.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

Figure 1:
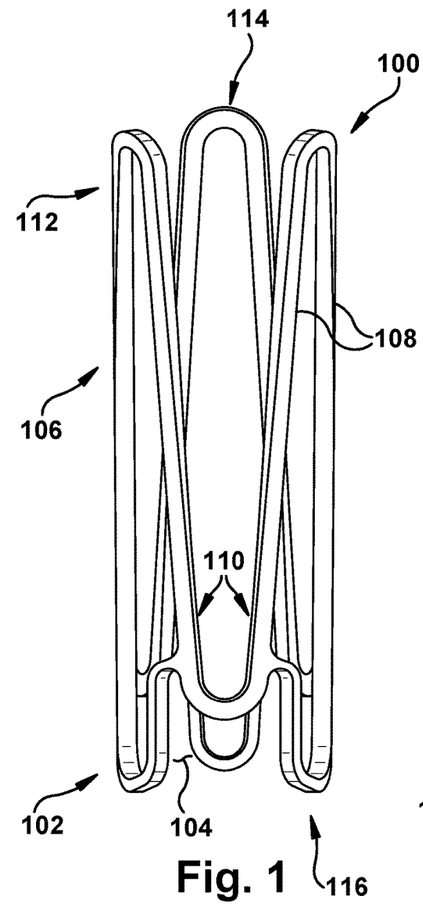
FIG. 1 is a side view of an aspect of the invention in a compressed condition.

FIG. 1 depicts a gradually-expandable stent 100, including a base ring 102, completely encircling a central valve-accepting area 104. A plurality of uprights 106 is provided. Each upright 106 includes two generally longitudinally extending upright struts 108. Each upright strut 108 has a strut base 110 directly connected to the base ring 102 and a strut tip 112 directly attached to the other strut tip 112 of the other upright strut 108 (of the same upright 106) to form a rounded upright apex 114. The upright apex 114 is longitudinally spaced from the base ring 102. The "longitudinal" direction, as referenced herein, is substantially in the vertical direction, in the orientation of FIGS. 1-2. The plurality of uprights 106 may be spaced equidistantly from one another around a circumference of the base ring 102.

At least one expansion feature 116 is associated with the base ring 102. The expansion features 116 gradually expand to enlarge the central valve-accepting area 104 toward a maximum valve-accepting area responsive to growth of the patient over an extended dwell time. For example, the dwell time could be a plurality of months, a plurality of years, a plurality of decades or any other desired length of time, as long as the dwell time is longer than a few months. For example, expansion of the expansion features 116 that occurs in conjunction with a discrete surgical procedure, such as expansion from a catheter-carried configuration to a use configuration for fastening to a valve annulus, would be too immediate to be considered as having occurred "over an extended dwell time".

Here, the dwell time is used to accommodate growth of a patient, which necessarily occurs over a longer period of time than that needed for a single surgical procedure. For example, in a Ross procedure, a pulmonary autograft is secured (e.g., via sutures) within the central valve-accepting aperture 104, and the entire assembly (of the stent 100 and pulmonary autograft combination) is secured (e.g., via sutures) within a valve annulus of an aortic or mitral valve. As the patient then grows and the valve annulus expands, the stent 100 will gradually expand along with the valve annulus, such as by radially outward pulling forces upon the sutures securing the stent 100 within the ring. A "radial" direction, as used herein, is a direction which is substantially perpendicular to, and emanating from, the longitudinal direction, such as the horizontal direction in the orientation of FIGS. 1-2.

This gradual expansion is facilitated by the expansion features 116, which may be of any suitable type(s) for a particular use application, and may be of any suitable design, including one or more of those described herein. Each expansion feature 116 may be interposed circumferentially between two adjacent uprights 106. A "circumferential" direction, as used herein, is a direction which is concentric to the longitudinal direction, such as around the circumference of the base ring 102 in the orientation of FIGS. 1-2. Each expansion feature 116 may form an integral part of the base ring 102.

Figure 2:
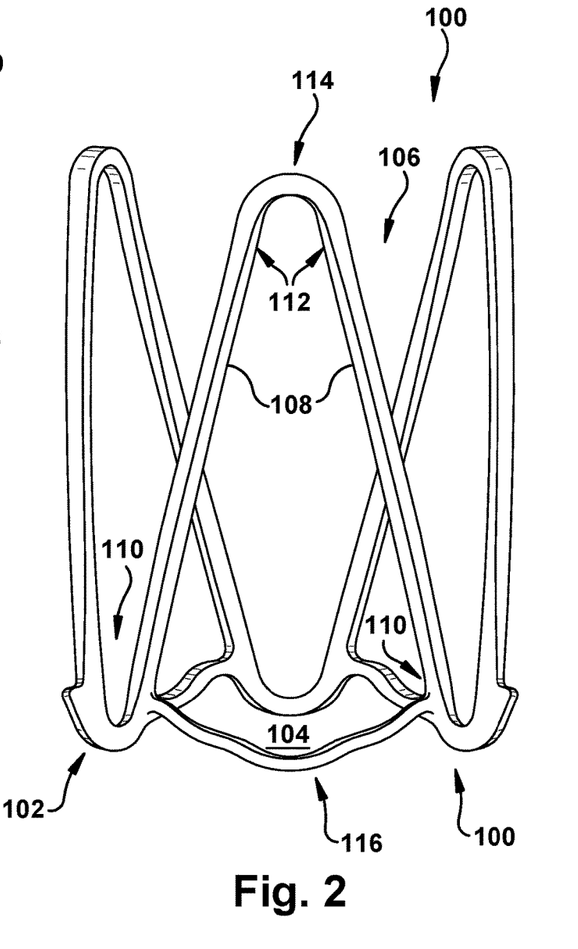
FIG. 2 is a side view of the aspect of FIG. 1 in an expanded condition.

As shown in the embodiment of FIGS. 1-2, at least one expansion feature 116 may include a U-bend (with the "open" side of the "U" opening either upward, as shown, or downward) having an initial closed condition, shown in FIG. 1, and an expanded open condition, shown in FIG. 2.

Figure 3:
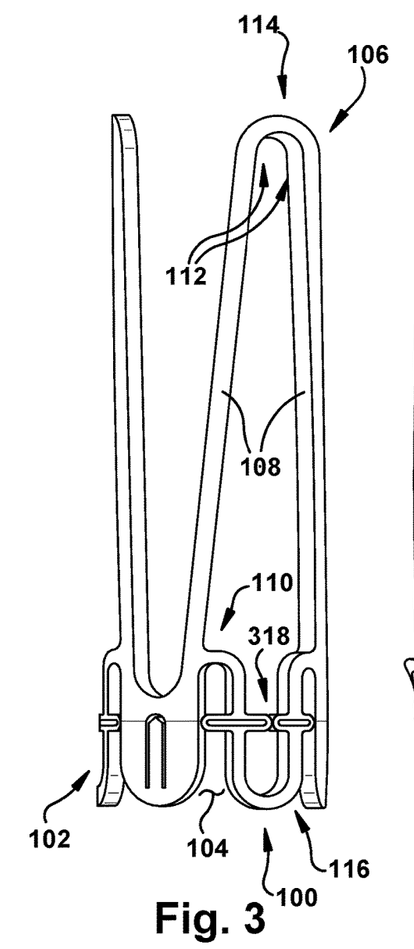
FIG. 3 is a side view of an aspect of the invention in a compressed condition.
Figure 4:
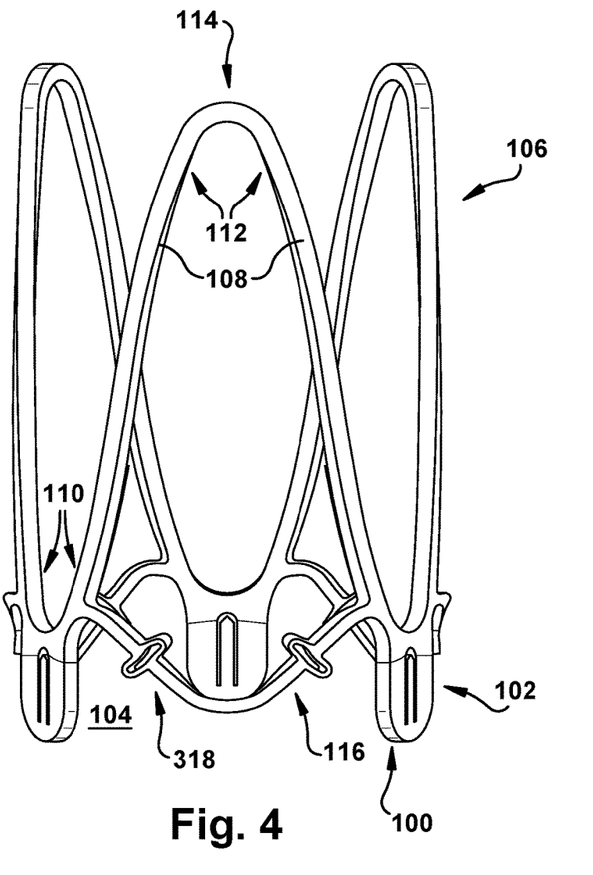
FIG. 4 is a side view of the aspect of FIG. 3 in an expanded condition.

As shown in the embodiment of FIGS. 3-4, at least one expansion feature may include an apertured frame 318 having an initial elongated condition (shown in FIG. 3, where the apertured frame 218 has a small, slit-like aperture) and an expanded rounded condition (shown in FIG. 4, where the apertured frame is "opened" by the opposing sides thereof being pulled circumferentially apart by the adjacent base ring 102 beams).

Figure 5:
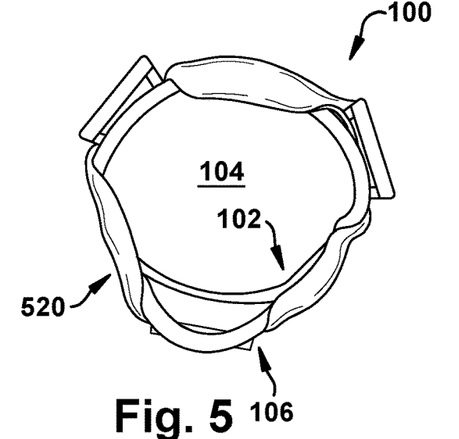
FIG. 5 is a top view of the aspect of FIG. 5 in an example use configuration.
Figure 6:
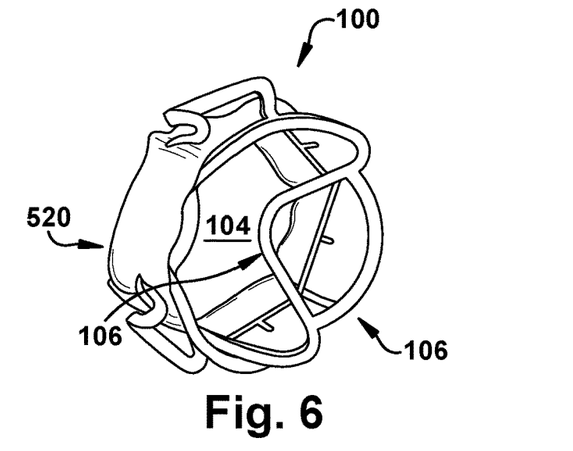
FIG. 6 is a bottom perspective view of the aspect of FIG. 5.

Turning to FIGS. 5-6, at least a portion of the stent 100—of any configuration—may be at least partially covered by a skirt 520 of flexible material of any desired type, including allograft tissue, autograft tissue, and/or synthetic material. The skirt 520, when present, may extend circumferentially about an inside or outside surface of the stent 100 (e.g., radially inside or outside the plurality of uprights 106). The skirt 520 may be secured to other stent 100 structures in any desired manner, such as, but not limited to, suturing to other stent 100 components. When present, the skirt 520 may be provided to assist with attachment of the stent 100 to the surrounding patient tissue (e.g., by promoting tissue ingrowth), for helping to seal the valve annulus, or for any other desired reason.

It is contemplated that, in some embodiments of the stent 100, the skirt 520 may serve both as a base ring 102 and as an expansion feature 116. The uprights 106 could be attached to (or otherwise carried by) the skirt 520, which would then stretch or flex to enlarge the diameter of the base ring 102.

As shown in the embodiments of FIGS. 7-10 and 11-18, at least one expansion feature 116 may include a beam 722 for selectively sliding radially with respect to a cuff 724. At least one cuff 724 is associated with each upright 106.

Figure 7:
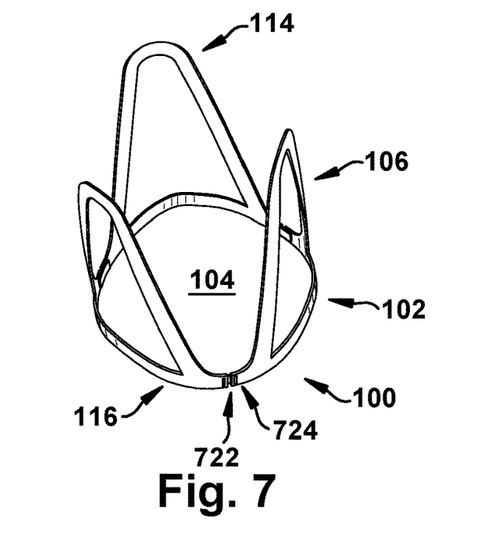
FIG. 7 is a top perspective view of an aspect of the invention in a compressed condition.
Figure 8:
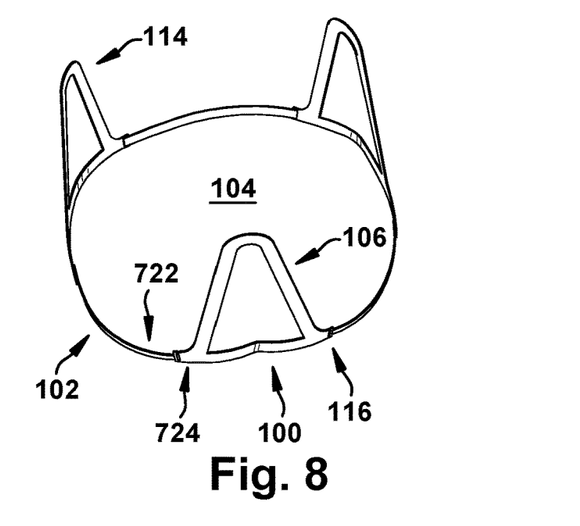
FIG. 8 is a top perspective view of the aspect of FIG. 7 in an expanded condition.
Figure 9:
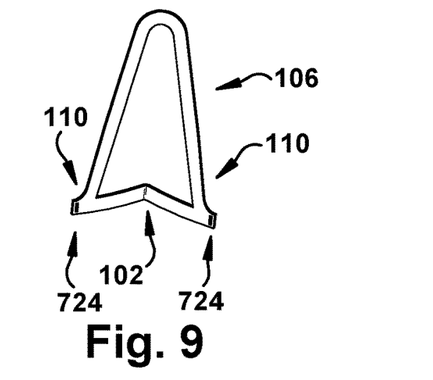
FIGS. 9-10 are side views of components of the aspect of FIG. 7.
Figure 10:
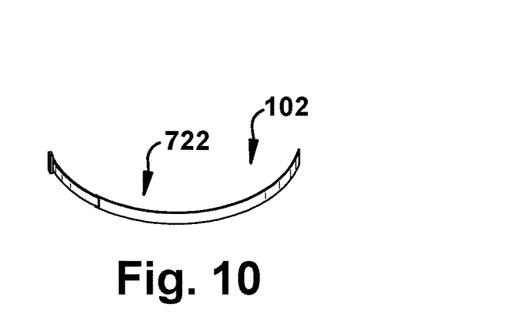

In the embodiment of FIGS. 7-10, each upright 106 is formed integrally (i.e., as a single-piece, unitary construct) with a portion of the base ring 102, as shown in FIG. 9. The remaining portions of the base ring 102, shown in FIG. 10, are then interposed circumferentially between two uprights 106. The cuffs 724 in the embodiment of FIGS. 7-10 are simple apertures near the strut bases 110, through which at least a portion of the beams 722 are slidably threaded. Optionally, and as shown in FIG. 10, the beams 722 can include a thickened or increased-height end, to prevent pullout from the cuffs 724. As shown in FIG. 7, the beams 722 can circumferentially overlap with the portions of the base ring 102 integrally formed with the upright 106. Then, under radially-oriented force, the beams 722 slide circumferentially with respect to the cuffs 724 to expand the diameter of the base ring 102, as shown in the sequence from FIG. 7 to FIG. 8.

Figures 11, 12, 13:
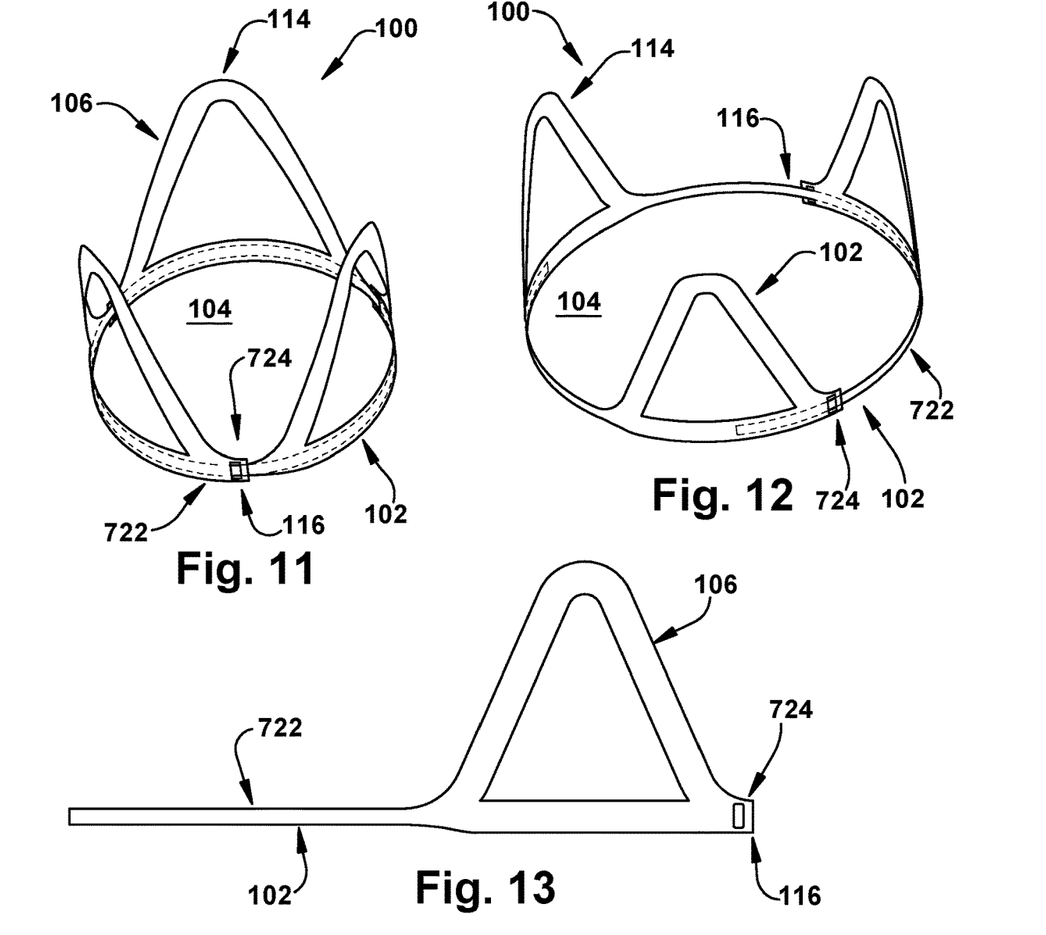
FIG. 11 is a top perspective view of an aspect of the invention in a compressed condition.
FIG. 12 is a top perspective view of the aspect of FIG. 11 in an expanded condition.
FIG. 13 is a side view of a component of the aspect of FIG. 11.

The embodiment of FIGS. 11-13 is similar to that of FIGS. 7-10, except that each upright 106 is formed integrally (i.e., as a single-piece, unitary construct) with both a cuff 724 and a beam 722), as shown in FIG. 13. A plurality of these FIG. 13 "upright 106 constructs" are daisy-chained into a linear series arrangement, with the beam 722 portions of one upright 106 construct being slidably threaded through the cuff 724 portions of a circumferentially adjacent upright 106 construct. Then, under radially-oriented force, the beams 722 slide circumferentially with respect to the cuffs 724 to expand the diameter of the base ring 102, as shown in the sequence from FIG. 11 to FIG. 12.

Figure 14:
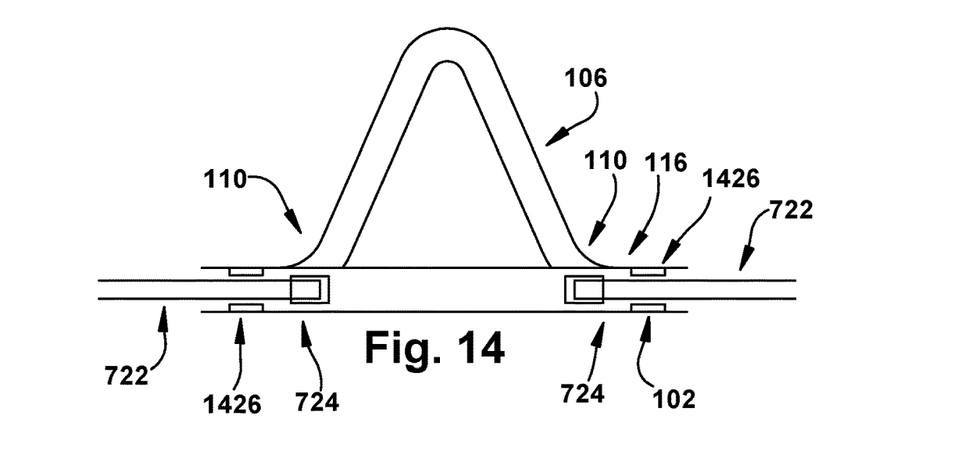

FIG. 14 illustrates schematically a portion of a slightly different stent 100 arrangement, wherein the portion of the base ring 102 which is located circumferentially between the strut bases 110 of the same upright 106 is at least partially tubular to provide a cuff 724 feature at each strut base 110. As shown in the telescoping arrangement of FIG. 14, a washer/spacer 1426 is located inside the tubular portion of the base ring 102 to narrow the cuff 724 area, so that the beam 722 (which may include a thickened end portion, as shown) resists "pulling out" from the cuff 724.

Figures 15, 16:
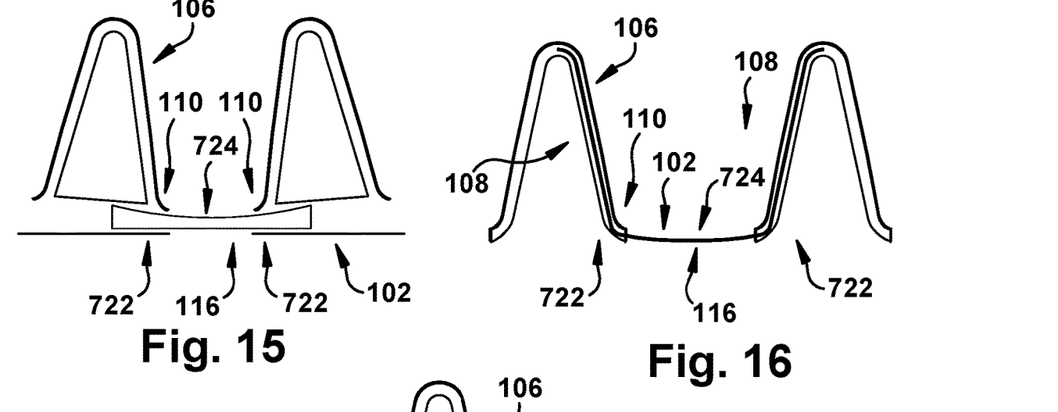

FIG. 15 illustrates schematically a portion of a stent 100 arrangement which telescopes, similar to the arrangement of FIG. 14. However, in FIG. 14, the longitudinal diameter of the tube at the cuff 722 portion of the base ring 102 is reduced to provide a frictional fit with the beam 724 portion. This reduced-diameter portion of the cuff 722 can assist with avoiding pull-out of the beam 724.

FIG. 16 illustrates schematically a portion of a stent 100 arrangement which telescopes, similar to the arrangements of FIGS. 14-15. However, in FIG. 16, the upright struts 108 themselves are tubular to serve as cuffs 722, and accept thereinto a portion of a wire serving at the beam 724. Here, the base ring 102 is discontinuous, having circumferential gaps between each adjacent pair of upright struts 108 forming a single upright 106. The length of the beam 724 wire itself resists pull-out from the cuffs 722, by being long enough that the beam 724 wires of a single stent collectively are significantly longer than a likely maximum expansion of the stent 100.

Figure 17:
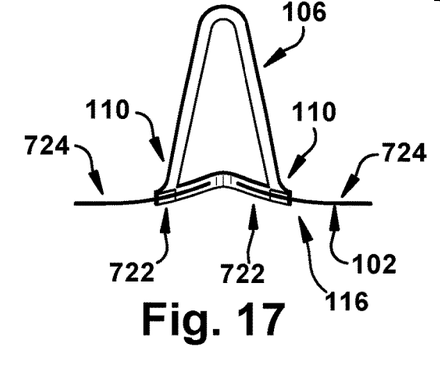

FIG. 17 illustrates schematically a portion of a stent 100 arrangement which telescopes, similar to the arrangements of FIGS. 14-16. However, in FIG. 17, the cuffs 722 are short tubes attached to the base ring near the strut bases 110, and the beam 724 is a wire which extends circumferentially into the cuff 722 tubes. As with the arrangement of FIG. 16, the beam 724 wires may simply be long enough that pullout is unlikely before the stent 100 reaches a maximum expansion. The cuffs 722 may also or instead be frictional-fit with the beam 724 wires to resist free sliding of the beam 724 within the cuffs 724, through an increased diameter of the wire near the ends and/or a tight fit of the cuffs 722 around the wire.

Figure 18:
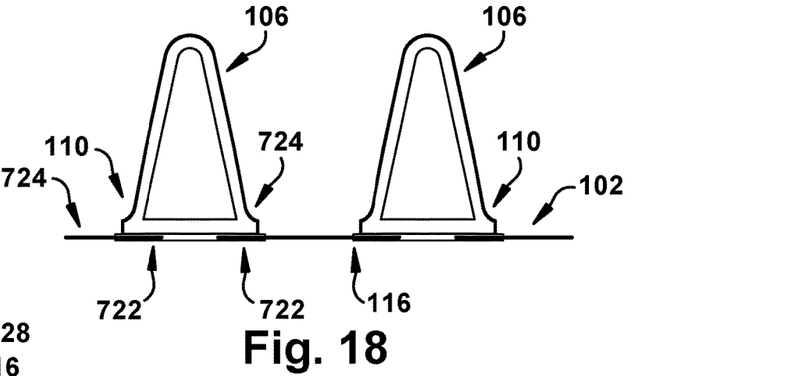

FIG. 18 illustrates schematically a portion of a stent 100 arrangement which telescopes, similar to the arrangements of FIGS. 14-17. However, in FIG. 18, the cuffs 722 are short tubes extending between adjacent strut bases 110 of a single upright 106, and the beam 724 is a wire which is anchored (e.g., via a frictional fit with a thickened portion at one end) in the cuff 722 of one upright 106, and which is permitted to slide with respect to the circumferentially adjacent cuff 722 of an adjacent upright 106. Effectively, the arrangement of FIG. 18 operates analogously to the arrangement of FIGS. 11-13.

The stent 100 of any arrangement of the present invention may be at least partially formed from a biodegradable material. When present the biodegradable material may be strategically placed to facilitate gradual expansion of the stent over time as the biodegradable material degrades. For example, at least a portion of the base ring 102 could be made of a biodegradable material which releases the base ring 102, upon degradation, to allow circumferential expansion of the base ring 102 under radial force.

Figure 19:
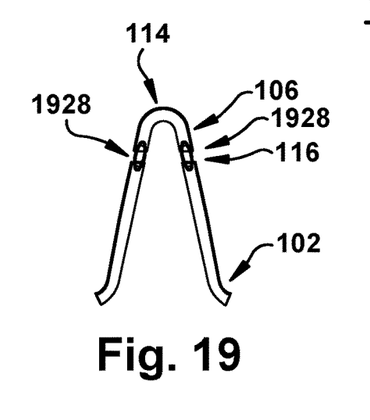
Figure 20:
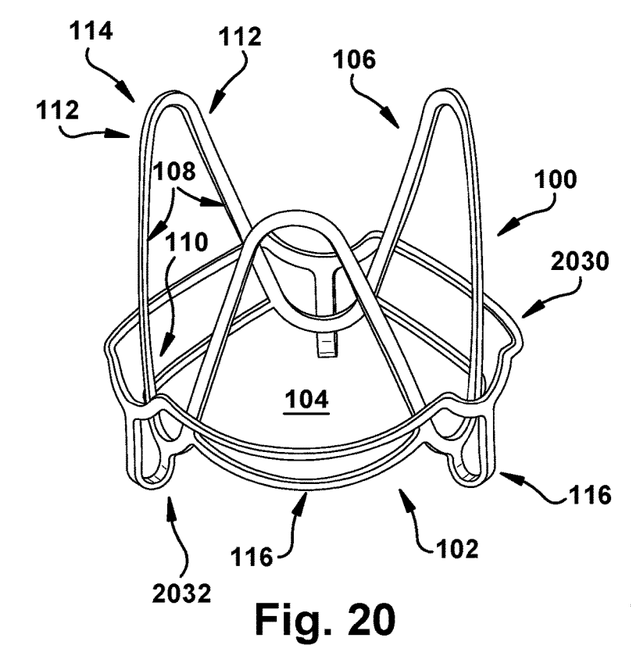
FIG. 20 is a top perspective view of an aspect of the invention in an expanded condition.
Figure 21:
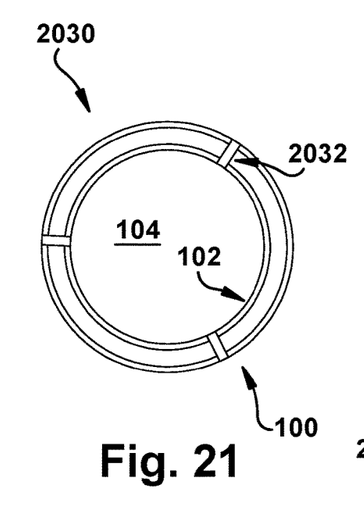
FIG. 21 is a bottom view of the aspect of FIG. 20.
Figure 22:
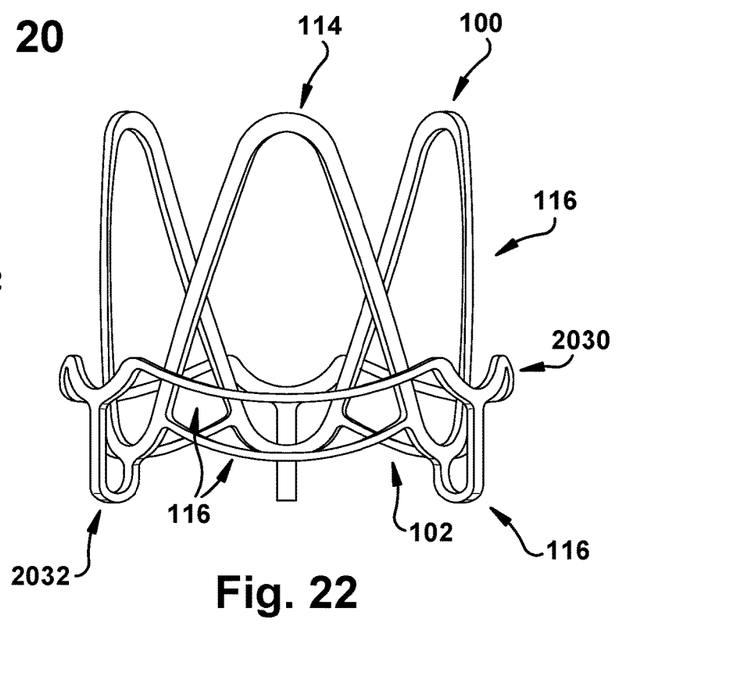
FIG. 22 is a side view of the aspect of FIG. 20.
Figure 23:
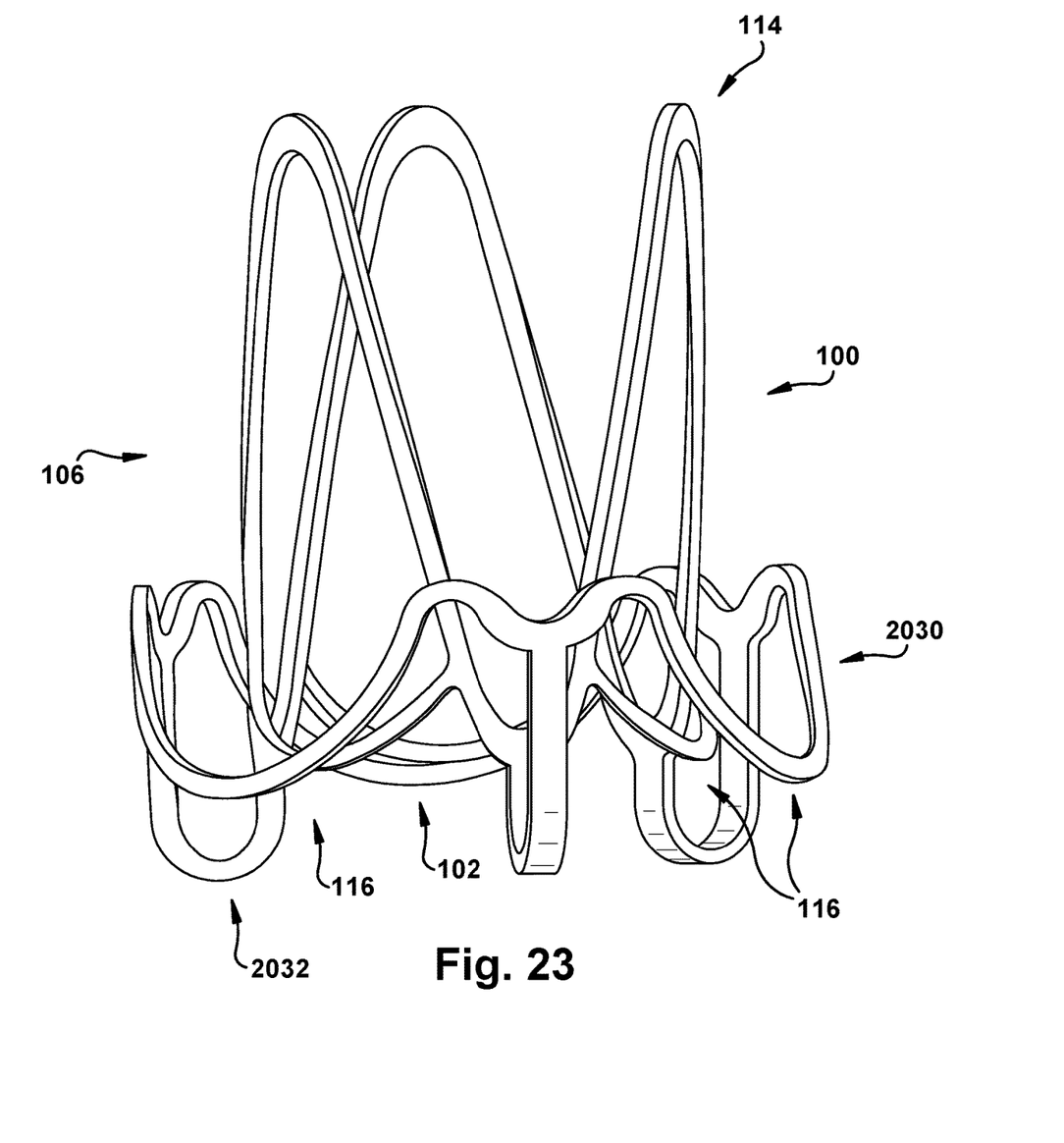
FIG. 23 is a side view of the aspect of FIG. 20 in a compressed condition.
Figure 24:
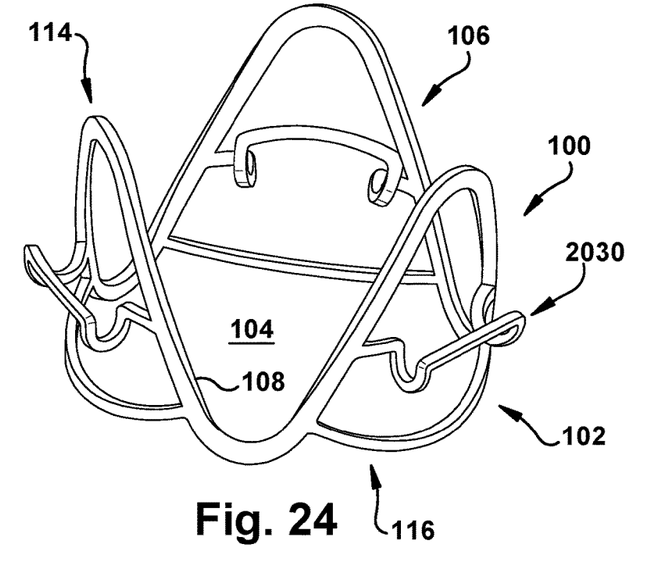
FIG. 24 is a top perspective view of an aspect of the invention in an expanded condition.
Figure 25:
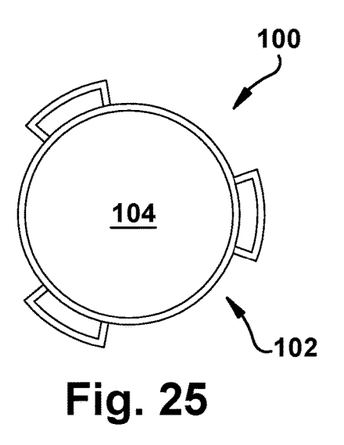
FIG. 25 is a bottom view of the aspect of FIG. 24.
Figure 26:
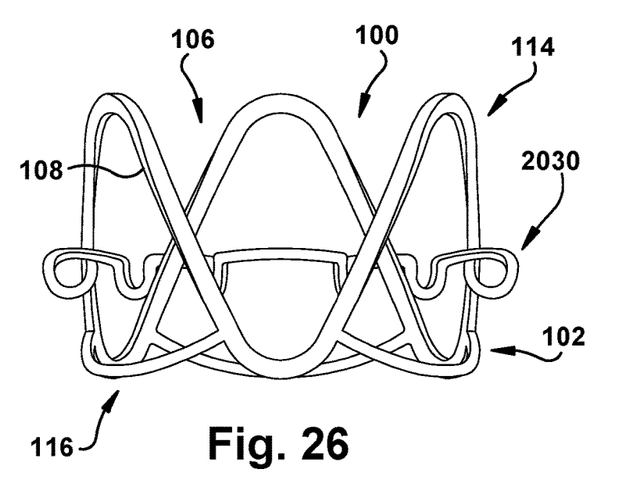
FIG. 26 is a side view of the aspect of FIG. 24.
Figure 27:
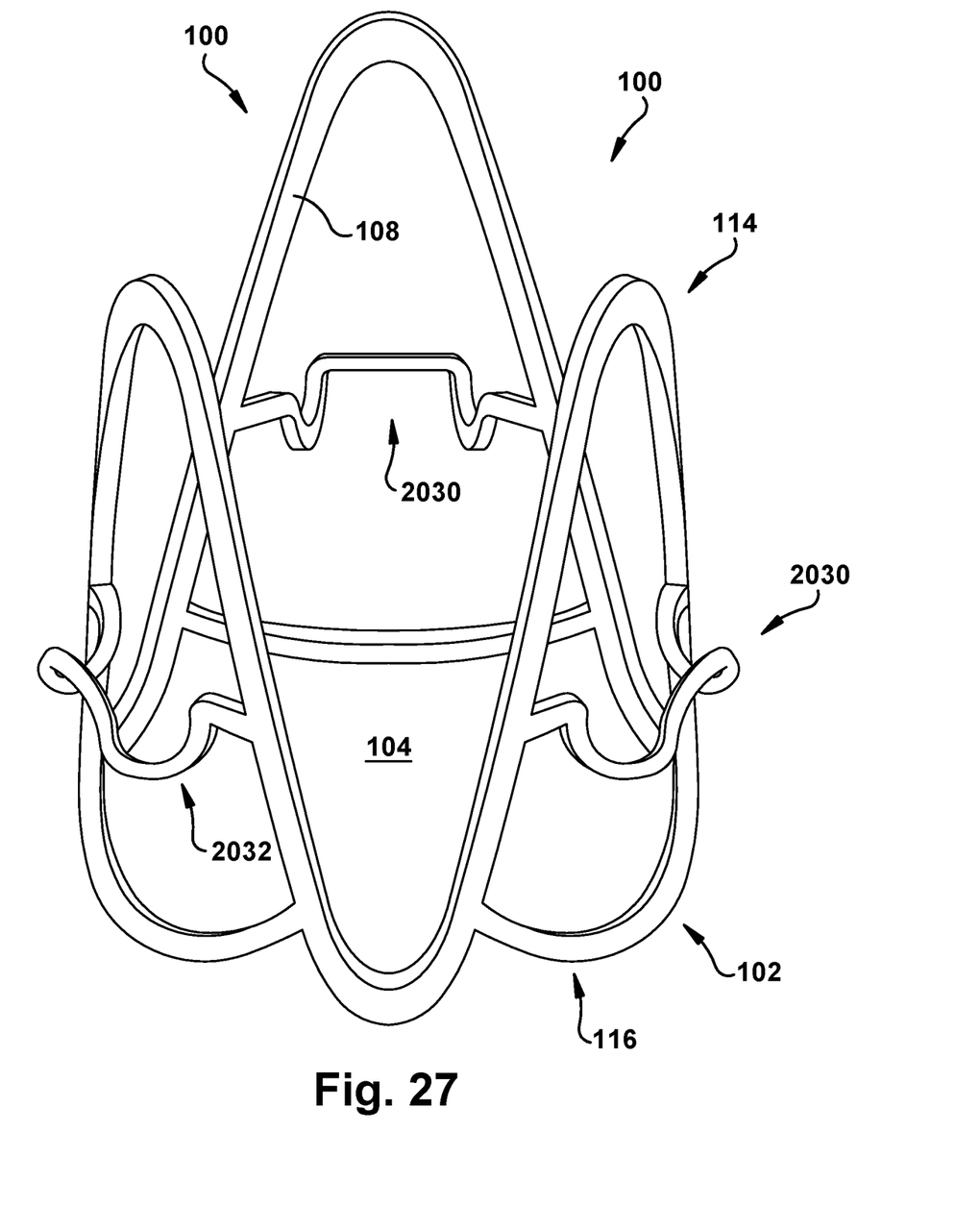
FIG. 27 is a side view of the aspect of FIG. 24 in a compressed condition.

At least one upright strut 106 could also or instead include a frangible portion 1928 including a biodegradable material, such as, but not limited to, a biodegradable suture connecting portions of the upright strut(s) 106 as shown in FIG. 19. The frangible portion 1928, when present, may permit selective longitudinal movement of the upright apex 114 with respect to the base ring 102 responsive to degradation of the biodegradable material of the frangible portion 1928. This may be particularly desirable when both the base ring 102 and the upright apices 114 of a single stent 100 are separately connected (directly or indirectly) to the adjacent patient tissue, which itself stretches longitudinally as the patient grows.

FIGS. 20-27 depict different aspects of stents 100 which include slightly different structures from the aspects shown in FIGS. 1-19, but also have many similar features to those previously described aspects.

As shown in FIGS. 20-23, a gradually-expandable stent 100 includes a base ring 102, completely encircling a central valve-accepting area 104. A plurality of uprights 106 is provided. Each upright 106 includes two generally longitudinally extending upright struts 108. Each upright strut 108 has a strut base 110 directly connected to the base ring 102 and a strut tip 112 directly attached to the other strut tip 112 of the upright strut 108 at a rounded upright apex 114. The upright apex 114 is longitudinally spaced from the base ring 102.

The stents 100 depicted in FIGS. 20-27 include at least one external ring feature 2030. The ring feature 2030 extends coaxially with the base ring 102 and is spaced laterally outside at least one upright 106. As shown in FIGS. 20-23, the external ring feature 2030 of this stent 100 extends completely around the base ring 102. In the FIGS. 24-27 embodiment, in contrast, a plurality of external ring features 2030 each extend partially circumferentially around the base ring 102. The external ring features 2030 may be configured in any desired manner, and provided for any desired reason, such as, but not limited to, providing valve annulus attachment points, helping attach the stent 100 to an adjacent native patient tissue (e.g., vessel) wall, limiting relative travel of adjacent struts 108, supporting the base ring 102, or any desired reason(s).

At least one expansion feature 116 is associated with at least one of the external ring feature 2030 and the base ring 102. The expansion features 116 gradually expand to enlarge the central valve-accepting area 104 toward a maximum valve-accepting area responsive to growth of the patient over an extended dwell time. In the aspect shown in FIGS. 20-23, both the external ring feature 2030 and the base ring 102 include expansion features 116 of the form of arc-shaped portions which "flatten out" to expand/extend and thus increase the distance between adjacent uprights 106 as the central valve-accepting area 104 enlarges. This "flattening" can be seen by comparing the compressed view of FIG. 23 to the expanded view of FIG. 20.

Alternatively, in the aspect shown in FIGS. 24-27, only the base ring 102 includes expansion features 116; the segment-type external ring features 2030 shown in FIGS. 24-27 instead simply travel further (circumferentially) apart as they are carried during the expansion of the base ring 102.

As shown in the embodiment of FIGS. 28-31, with similarities to the embodiments of FIGS. 7-10 and 11-18, at least one expansion feature 116 may include a beam 722 for selectively sliding radially with respect to a cuff 724. At least one cuff 724 is associated with each upright 106.

Figure 28:
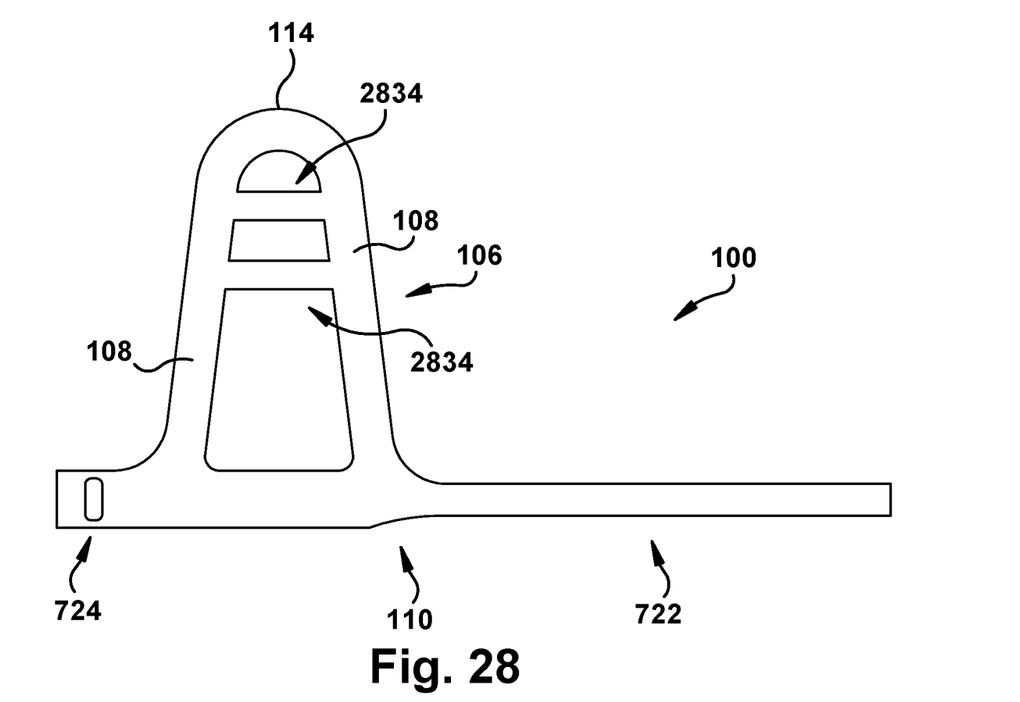
FIG. 28 is a side view of a component of an aspect of the invention.
Figure 29:
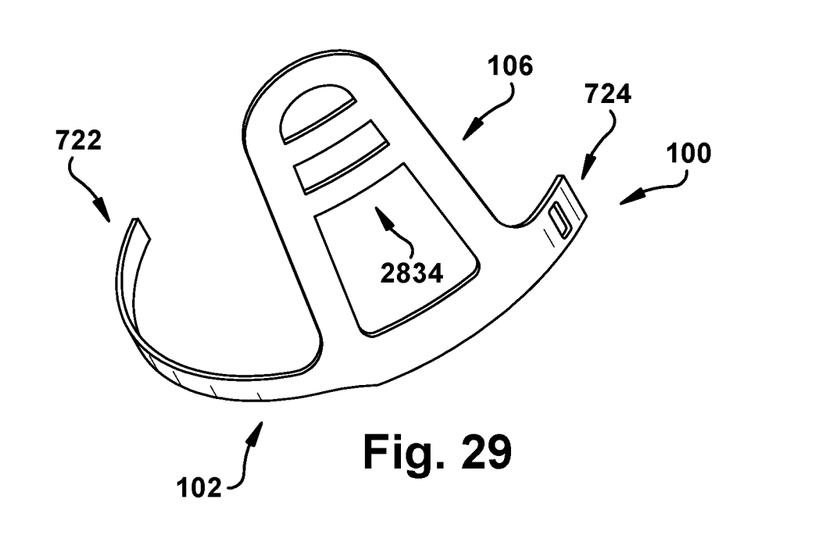
FIG. 29 is a perspective top view of the component of FIG. 28.

In the embodiment of FIGS. 28-31, each upright 106 is formed integrally (i.e., as a single-piece, unitary construct) with a portion of the base ring 102, as shown in FIG. 28. The cuffs 724 in the embodiment of FIGS. 28-31 are simple apertures near the strut bases 110, through which at least a portion of the beams 722 are slidably threaded. Optionally, and as shown in FIG. 28, the beams 722 can have a smaller height than a portion of the base ring 102 including the cuff 724, to allow vertical space for the aperture-type cuff 724.

Also apparent from FIGS. 28-31 is the crossbrace 2834 (two shown for each upright 106). The crossbrace(s) 2834, of which any number and configuration may be provided, serve to prevent widening of the upright 106 due to pivotal movement of the upright struts 108 around the connecting upright apex 114. Therefore, radial expansion of the stent 100 over the extended dwell time will be substantially accomplished via expansion of the base ring 102.

Similar to previously described embodiments, under radially-oriented force, the beams 722 of the embodiment of FIGS. 28-31 slide circumferentially with respect to the cuffs 724 to expand the diameter of the base ring 102. A plurality of these FIG. 28 "upright 106 constructs" are daisy-chained into a linear series arrangement, with the beam 722 portions of one upright 106 construct being slidably threaded through the cuff 724 portions of a circumferentially adjacent upright 106 construct. Then, under radially-oriented force, the beams 722 slide circumferentially with respect to the cuffs 724 to expand the diameter of the base ring 102.

Figure 30:
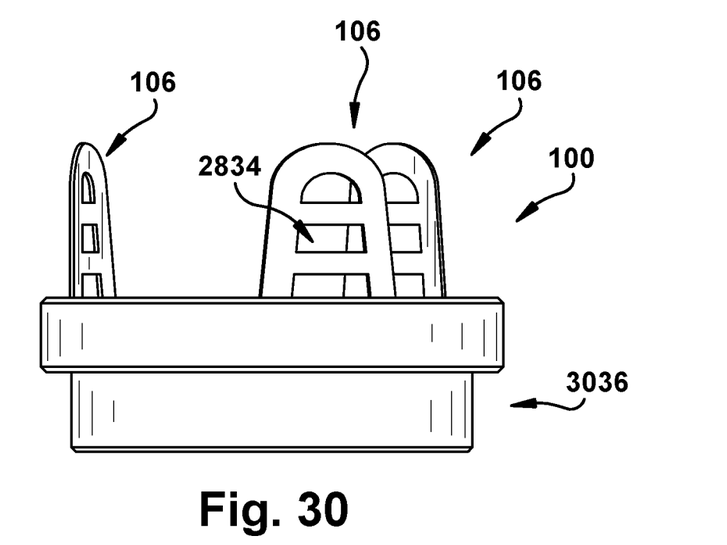
FIG. 30 is a side view of the component of FIG. 28 in an example use configuration.
Figure 31:
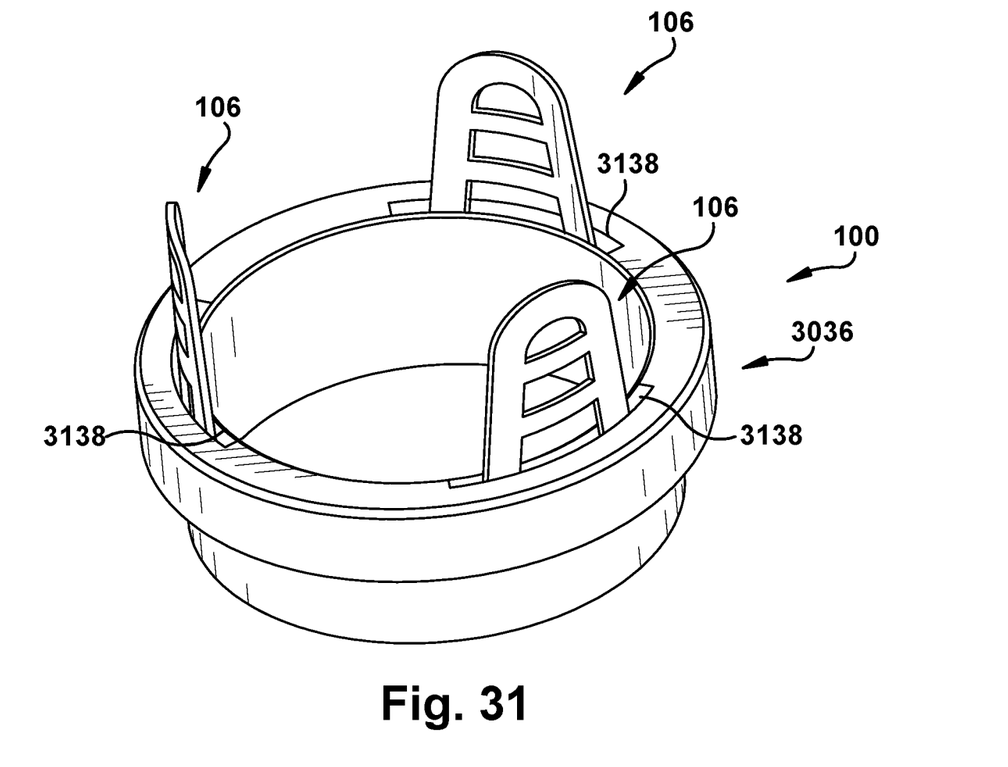
FIG. 31 is a perspective top view of the component of FIG. 28 in the example use configuration of FIG. 30.

With reference to FIGS. 30-31, a sewing cuff 3036, which may be used with any of the embodiments of the stent 100 herein, is provided. The sewing cuff 3036, which may be either substantially rigid or at least partially flexible, may be used to provide an enclosed area within which the base ring 102 is at least partially located, in order to discourage direct tissue ingrowth to the base ring 102 and facilitate expansion of the base ring 102 as desired over the extended dwell time, without interference from nearby body tissues. For example, the sewing cuff 3036 could be sutured into the patient's valve annulus during the initial implantation procedure. The sewing cuff 3036 could then support the uprights 106 and allow some degree of radial movement of the uprights 106, since the uprights 106 extend upward through upright slits 3138 cut in the sewing cuff 3036. Since there is some room on one or both sides of the uprights 106 for motion along/within the upright slits 3138, expansion of the stent 100 can occur in a relatively orderly fashion, guided by the sewing cuff 3036, where provided.

As shown in the Figures, the stent 100 may also include at least one suspension feature 2032 cantilevering the at least one external ring feature 2030 laterally outward from at least one of the base ring 102 and at least one upright 106.

Optionally, the suspension feature(s) 2032 may also expand or contract in a radial direction, substantially toward and away from the base ring 102, in order to facilitate differential expansion of the base ring 102 and the external ring feature 2030, when desired.

In use, the gradually-expanding stent 100 can be employed similarly for supporting a pulmonary autograft in a selected one of the mitral and aortic positions relative to a heart valve replacement procedure for a growth-potential patient. A gradually-expandable stent 100 (of any embodiment, configuration, or arrangement following the principles of the present invention, whether or not shown and/or described explicitly herein) is provided. The patient's heart is accessed in any desired manner, including using open and/or minimally invasive surgical techniques. The pulmonary autograft valve is harvested in any suitable manner, and a replacement valve (which could be made in any suitable manner, and using any desired natural and/or artificial tissues) is installed in place of the harvested pulmonary autograft valve.

At least one pulmonary autograft valve commissure of the pulmonary autograft valve is attached to an upright 106, in any desired manner, to secure the pulmonary autograft within the central valve-accepting area 104. Each upright 106 is attached, directly or indirectly, to a heart tissue at the selected one of the mitral and aortic portions to suspend the pulmonary autograft in a replacement position for a selected mitral or aortic valve. The surgical procedure is then completed, in any desired manner, and the patient, hopefully, resumes normal life.

Then, over an extended dwell time, the at least one expansion feature 116 is gradually actuated to enlarge the central valve-accepting area 104 toward a maximum valve-accepting area responsive to growth of the patient. This extended dwell time could be a period of weeks, months, or even years after the installation surgical procedure. Actuation of the expansion features 116 can be accomplished in any desired manner, including, but not limited to, using one or more of the mechanisms shown and described herein, or any other desired expansion feature 116 configuration. Accordingly, a gradually-expanding stent 100 can assist with a Ross procedure in a juvenile patient and help postpone or even avoid the necessity for re-operation (and the attendant risks) to replace a now-too-small valve as the patient grows.

It is contemplated that one or more radiopaque or otherwise detectable markers could be provided, on any desired portion of the stent 100, in order to facilitate location and/or visualization of the stent 100 within the patient's body.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A gradually-expandable stent, comprising:
   a base ring, completely encircling a central valve-accepting area;
   a plurality of uprights, each upright including two longitudinally extending upright struts, each upright strut having a strut base integrally formed with a portion of the base ring and a strut tip directly attached to the other strut tip of the upright strut at a rounded upright apex, the upright apex being longitudinally spaced from the base ring, each upright also including at least one crossbrace extending radially between adjacent upright struts of a chosen upright; and
   at least one expansion feature associated with the base ring, the expansion feature including a beam integrally formed with a selected upright for selectively sliding radially with respect to a cuff integrally formed with an other upright, the expansion feature gradually expanding to enlarge the central valve-accepting area toward a maximum valve-accepting area responsive to growth of the patient over an extended dwell time.

2. The stent of claim 1, being at least partially formed from a biodegradable material, the biodegradable material being strategically placed to facilitate gradual expansion of the stent over time as the biodegradable material degrades.

3. The stent of claim 1, wherein the dwell time is a plurality of years.

4. The stent of claim 1, wherein the plurality of uprights are each spaced equidistantly from one another around the base ring.

5. The stent of claim 1, including a plurality of expansion features and wherein each expansion feature is interposed circumferentially between two adjacent uprights.

6. The stent of claim 1, wherein the at least one expansion feature forms an integral part of the base ring.

7. The stent of claim 1, wherein at least one expansion feature includes a beam for selectively sliding radially with respect to a cuff, at least one cuff being associated with each upright.

8. A gradually-expandable stent, comprising:
a base ring, completely encircling a central valve-accepting area;
a plurality of uprights, each upright including two longitudinally extending upright struts, each upright strut having a strut base directly connected to the base ring and a strut tip directly attached to the other strut tip of the upright strut at a rounded upright apex, the upright apex being longitudinally spaced from the base ring;
at least one external ring feature, extending coaxially with the base ring and spaced laterally outside at least one upright; and
at least one expansion feature associated with at least one of the external ring feature and the base ring, each expansion feature gradually expanding to enlarge the central valve-accepting area toward a maximum valve-accepting area responsive to growth of the patient over an extended dwell time;
wherein each upright strut has a strut base integrally formed with a portion of the base ring, and the expansion feature includes a beam integrally formed with a selected upright for selectively sliding radially with respect to a cuff integrally formed with an other upright.

9. The stent of claim 8, being at least partially formed from a biodegradable material, the biodegradable material being strategically placed to facilitate gradual expansion of the stent over time as the biodegradable material degrades.

10. The stent of claim 8, wherein the dwell time is a plurality of years.

11. The stent of claim 1, wherein the beam of at least one expansion feature is a smaller height than a portion of the base ring including the cuff.

12. The stent of claim 1, wherein each upright is formed integrally with a base ring segment and an expansion feature including a beam and a cuff to create an upright/base unit, the stent being comprised of a plurality of daisy-chained upright/base units mutually connected by the beam and cuff of adjacent ones thereof.

13. The stent of claim 12, wherein each upright/base unit is planar before being assembled into mutual connection with at least one other upright/base unit.

14. The stent of claim 1, wherein the beam has a height which is larger than a thickness of the beam.

15. The stent of claim 8, wherein the beam of at least one expansion feature is a smaller height than a portion of the base ring including the cuff.

16. The stent of claim 8, including at least one crossbrace extending radially between adjacent upright struts of a chosen upright.

17. The stent of claim 8, wherein each upright is formed integrally with a base ring segment and an expansion feature including a beam and a cuff to create an upright/base unit, the stent being comprised of a plurality of daisy-chained upright/base units mutually connected by the beam and cuff of adjacent ones thereof.

18. The stent of claim 17, wherein each upright/base unit is planar before being assembled into mutual connection with at least one other upright/base unit.

19. The stent of claim 8, wherein the beam has a height which is larger than a thickness of the beam.

* * * * *